United States Patent [19]

Giles et al.

[11] Patent Number: 4,997,770

[45] Date of Patent: Mar. 5, 1991

[54] METHOD AND MEANS FOR DETECTING BLOOD ALCOHOL IN HUMANS BY TESTING VAPOR ABOVE THE EYE

[75] Inventors: Howel G. Giles, Willowdale; Yedy Israel, Toronto, both of Canada

[73] Assignee: Alcoholism and Drug Addiction Res. Foundation

[21] Appl. No.: 151,306

[22] Filed: Feb. 1, 1988

[30] Foreign Application Priority Data

May 26, 1987 [CA] Canada .................................. 538,052

[51] Int. Cl.[5] ............................................. G01N 33/00
[52] U.S. Cl. .................................... 436/132; 128/645; 422/83; 436/900
[58] Field of Search ................ 436/132, 900; 128/645, 128/632, 635

[56] References Cited

U.S. PATENT DOCUMENTS

| | | | |
|---|---|---|---|
| 4,220,158 | 9/1980 | Delphy et al. ....................... | 128/632 |
| 4,401,122 | 8/1983 | Clark ..................................... | 128/632 |
| 4,461,303 | 7/1984 | Refojo et al. ....................... | 128/632 |
| 4,597,392 | 7/1986 | Opitz et al. .......................... | 128/635 |
| 4,809,698 | 3/1989 | Kogo .................................... | 128/632 |

FOREIGN PATENT DOCUMENTS 2506175 8/1976 Fed. Rep. of Germany ...... 128/632

OTHER PUBLICATIONS

Giles et al., "Measuring Alcohol In Vapours Above The Eye", *The Lancet*, 9/5/87, pp. 580–581.
Giles et al., "Noninvasive Estimation of Blood Alcohol Concentrations: Ethanol Vapor Above The Eye", *Alcoholism Clinical & Exp. Res.*, vol. 12, No. 2, Mar./Apr. 1988.
Giles et al., "Ethanol Vapours Above Lacrinal Fluid in the Rabbit" Canadian Journal of Physiology and Pharmacology, 12/87, pp. 2491–2493.
Giles et al., Can. J. Physiol. Pharmacol. 65 (12), 1987. pp. 2491–2493.
Giles et al., Alcohol Clin. Exp. Res. 12(2) 1988. pp. 255–258.

*Primary Examiner*—Robert J. Warden
*Assistant Examiner*—Lyle Alfandary-Alexander
*Attorney, Agent, or Firm*—Wood, Herron & Evans

[57] ABSTRACT

A method of detecting ethanol in lachrymal fluid is provided in which an open eye of a subject is enclosed in a chamber to define a space above the eye, an ethanol vapor sensor is introduced into the space of the chamber in a spaced relation to the eye; the sensor is calibrated; and the ethanol vapor concentration in the said lachrymal fluid exuded by the eye is measured.

20 Claims, 8 Drawing Sheets

ETHANOL TREATED RABBITS   FIG. 8

FIG. 9 STANDARD CORRELATING CURVE

FIG. 10 PLASMA CONC. COMPARISON

METHOD AND MEANS FOR DETECTING BLOOD ALCOHOL IN HUMANS BY TESTING VAPOR ABOVE THE EYE

BACKGROUND OF THE INVENTION

The present invention relates to the detection of alcohol in a human and more particularly to methods and means for such detection.

The detection of blood alcohol levels in human beings has been achieved by various methods and for different purposes.

For law enforcement the determination of blood alcohol levels has been essential for the prosecution of various offences particularly highway driving offences where the suspect may be impaired.

For general medical purposes it is frequently essential for the physicians to make an objective determination of the alcohol blood level of a patient to determine the health of the patient and/or the appropriate treatment.

Sometimes the purposes overlap such as in a highway traffic accident However, irrespective of the purposes, in the latter situation where the patient is critically ill the measurement of the alcohol blood level is by present methods time consuming and requires considerable expertise and is not possible without invasive methods.

The obtaining of a blood alcohol reading by the breathalyser technique will not give an accurate reading if the patient has only just finished consuming alcohol: the alcohol in the mouth distorts the reading.

The patient may have vomited or regurgitated as a consequence of the accident with the same effect or so that the patient cannot apply the breathalyser tube to his mouth. Or the patient may be unconscious so that a breathalyser reading may not be feasible.

The other present methods and equipment are more cumbersome and awkward to use so that they are, for the purpose of the present discussion irrelevant.

SUMMARY OF THE PRESENT INVENTION

Accordingly, it is an object of the present invention to provide a method and apparatus which enables the blood alcohol level in a patient to be determined objectively and independently of the remaining physical conditions of the patient.

It is a feature of the invention that the blood alcohol level of the patient is determined by measuring the ethanol vapor emitted by the patient's eye. This vapor is not contaminated by any alcohol or vomit in the victim's mouth and can be sampled even when the victim is unconscious if the eye is kept open, for example with available sterile adhesive strips.

There is therefore provided in accordance with the present invention:

An eyepiece having a substantially impervious wall defining a chamber with lower and upper open ends, said lower open end having edge matchingly conformable with the adjacent face contour, said upper open end being shaped to receive in use an ethanol detecting sensor, in substantially sealed, spaced relation with an eye of a subject.

There is also provided in accordance with present invention, a method of detecting ethanol in lachrymal fluid which comprises enclosing an open eye of a subject in a chamber to define a space above the eye, introducing an ethanol vapor sensor into the space of the chamber in a spaced relation to the eye; calibrating said sensor; and measuring the ethanol vapor concentration in said lachrymal fluid exuded by the eye.

Figure 1:
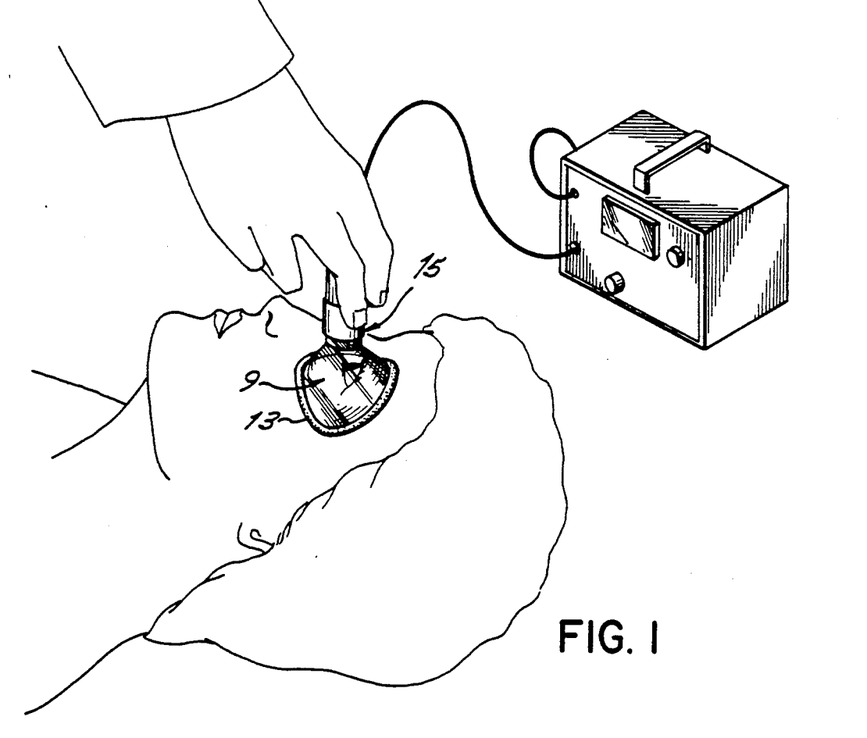
FIG. 1 is a general schematic view of a patient having blood alcohol level determined in accordance with the invention.

As illustrated in FIG. 1 the method of the present invention provides a non-invasive passive technique for determining the alcohol level in the subject's body fluids through a determination of the alcohol in the eye vapor.

The only important factor is that the eye of the subject be open. The eye vapor is not subject to contamination by mouth alcohol or by stomach gases due to regurgitation, as is the case with the breathalyser technique.

It is also apparent that the method may be applied when the patient is unconscious or not capable of taking any objects into the mouth.

Figure 2:
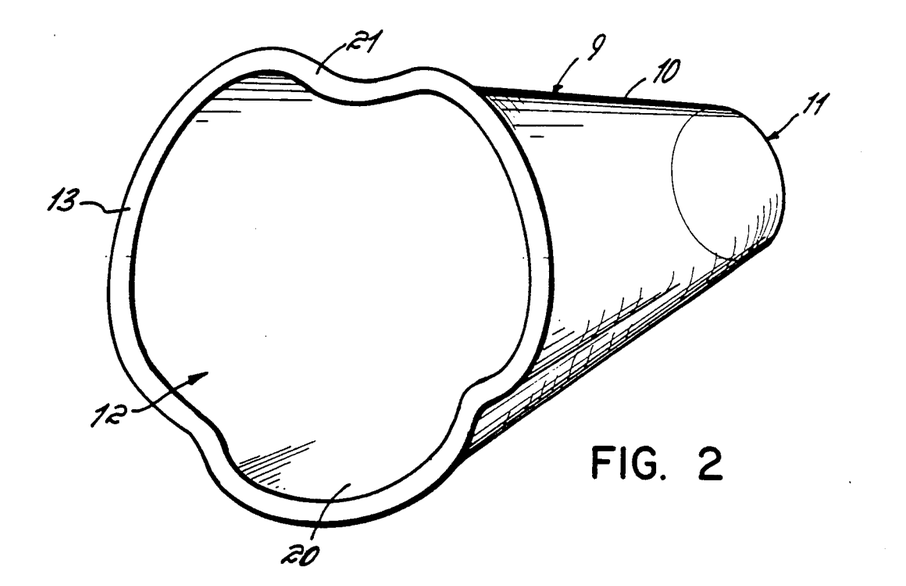
FIG. 2 is a general perspective view of an eyepiece in accordance with the present invention.

As shown in FIG. 2 an eyepiece 9 in the embodiment employed is a transparent plastic wall 10 having open upper and lower edges 11 and 12 defining openings. Around lower edge 12 a cushion 13 is provided. It will be observed that the lower edge 12 is relieved at substantially opposed sides 20 and 21 to conform with the adjacent cheek and nose surfaces with which it may come into contact. It will also be noted that this configuration permits use on either the right or left eye.

It will also be observed from FIG. 1 that a vapor sensor 15 is inserted through the upper opening 11 and held there so that it is spaced away from the adjacent eye surface. The spacing from the eye surface has been found to lead to a "cleaner" signal with less extraneous "noise".

Figure 3:
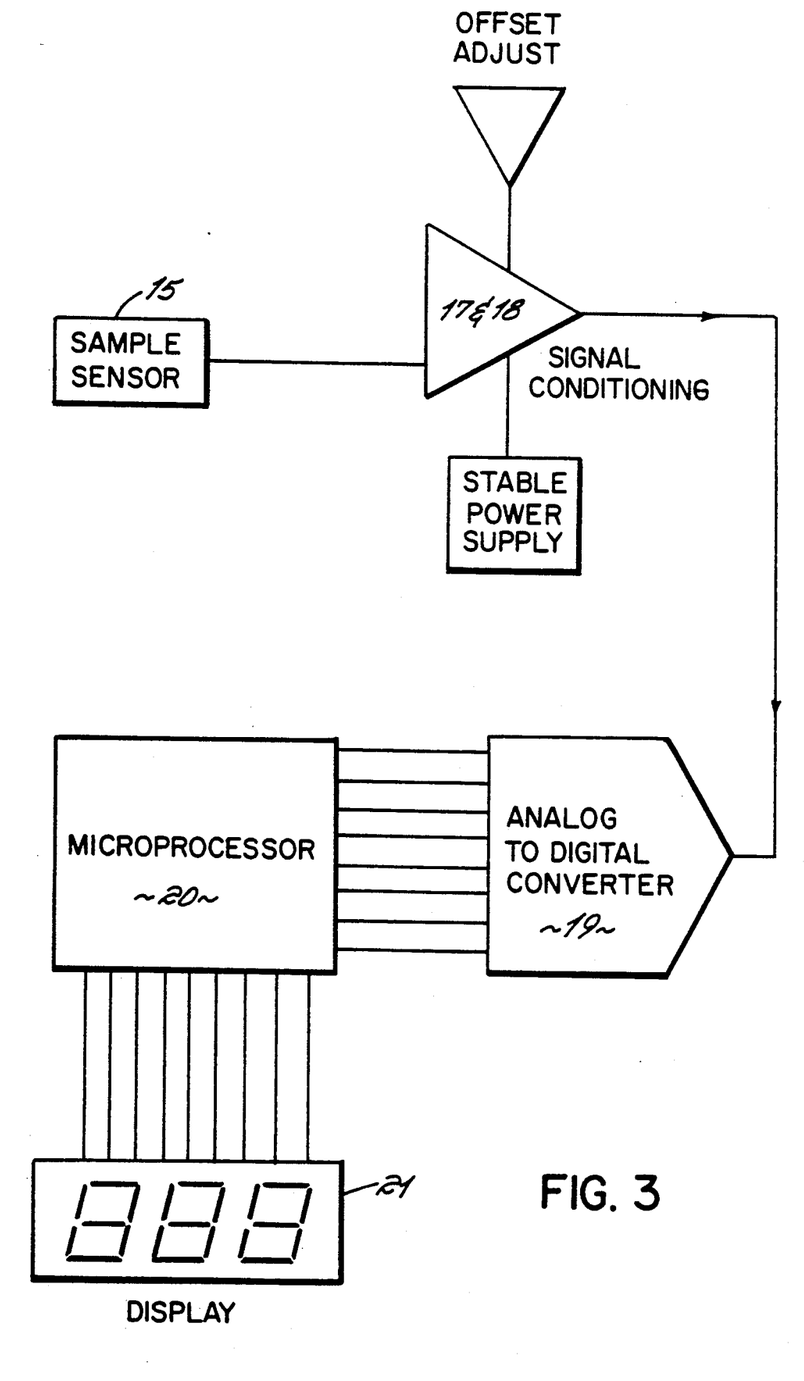
FIG. 3 is a block diagram of a circuit employed in the present invention.
Figure 4:
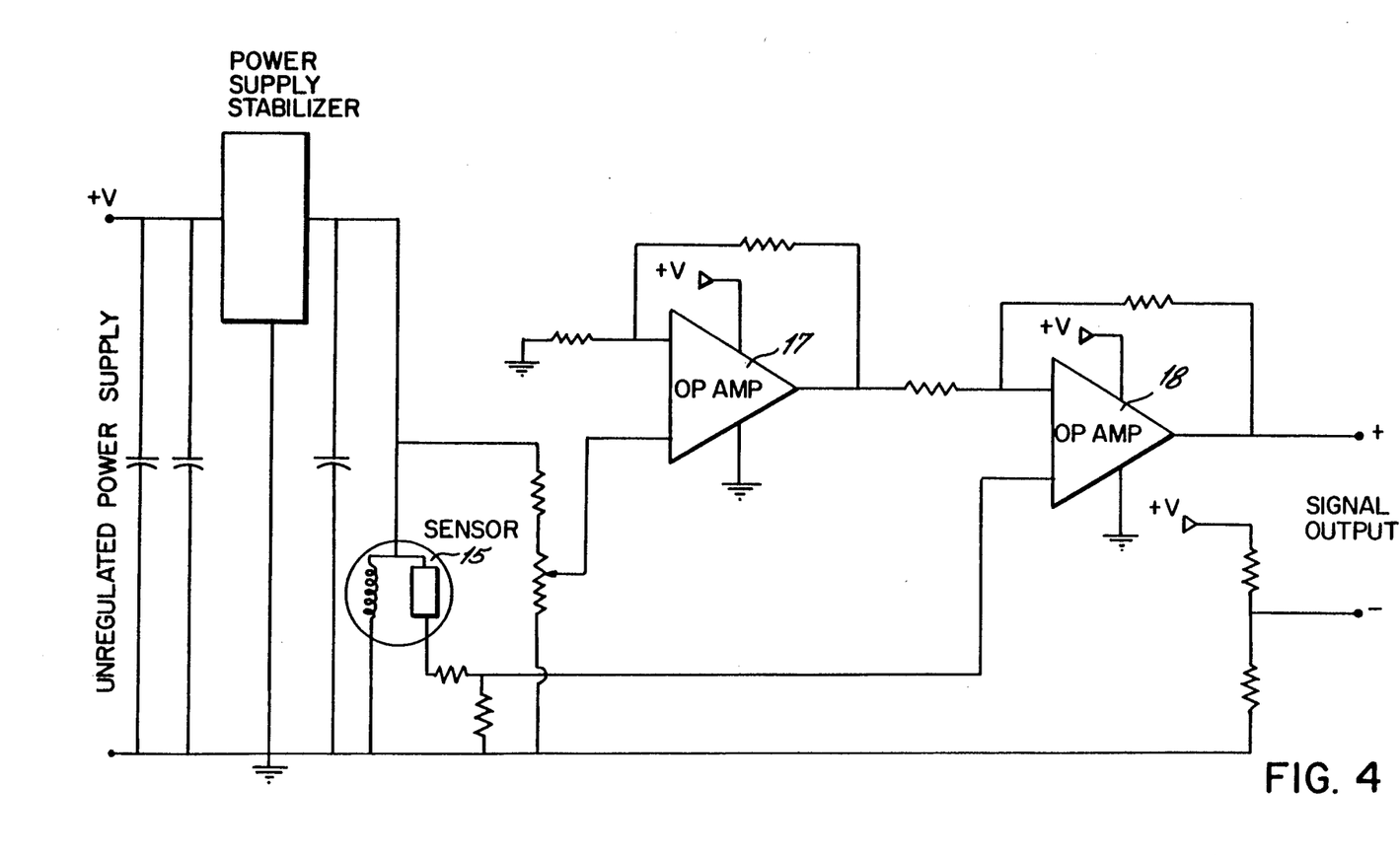
FIG. 4 is a schematic diagram of the circuit of FIG. 3.

As illustrated in FIGS. 3 and 4 the circuit employed comprises a vapor sensor such as a Type 812 Figaro gas sensor indicated at 15. The output of sensor 15 is connected through a pair of amplifiers 17 and 18 to an analog to digital converter 19, the output of the converter is connected to a microprocessor 20, and in turn to a digital display 21.

It will of course be understood that the sensor 16 is suitably calibrated prior to use. This may be provided by a reference sensor circuit depending upon the experimental conditions.

While it is recognized that intact excretion of ethanol takes places through urine and in vapor form through the breath, it was postulated that since ethanol was distributed throughout the total body water, lachrymal fluid should also contain ethanol at the same concentration as the remaining body fluid and since, according to Henry's law the concentration of ethanol in the vapor phase is proportional to the concentration of ethanol in the liquid phase a determination of ethanol in the lachrymal eye vapor would give an indication of the alcohol concentration in the subject's body fluids.

The invention will be more fully understood by reference to the following Examples and experiments.

EXAMPLE I

Normal Rats-Eye Vapor Response

Figure 5:
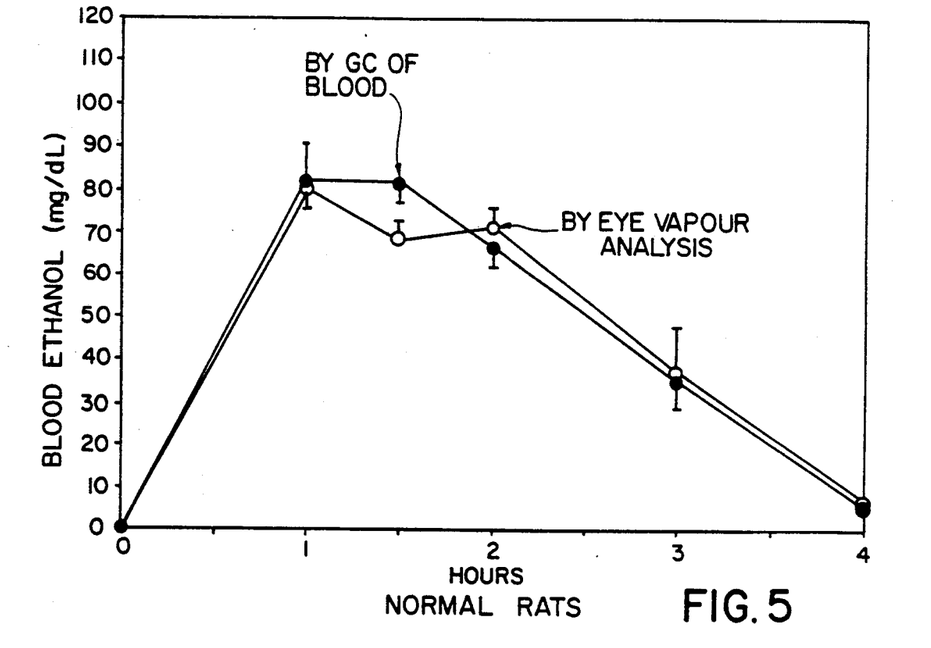
FIG. 5 is a diagram of illustrating the concentration of ethanol/time profile by gas chromatographic analysis of blood, and eye vapor analysis, respectively, in normal rats.

Male, Sprague-Dawley rats, weight 288 ±9 g, mean± s.e.m., were given ethanol, 1 g/kg, by gavage, as a 13% solution in water. Blood samples (0.05 ml) and eye vapor measurements were taken over four hours after ethanol administration. The results are illustrated in FIG. 5.

Ethanol Treated Rats

Figure 6:
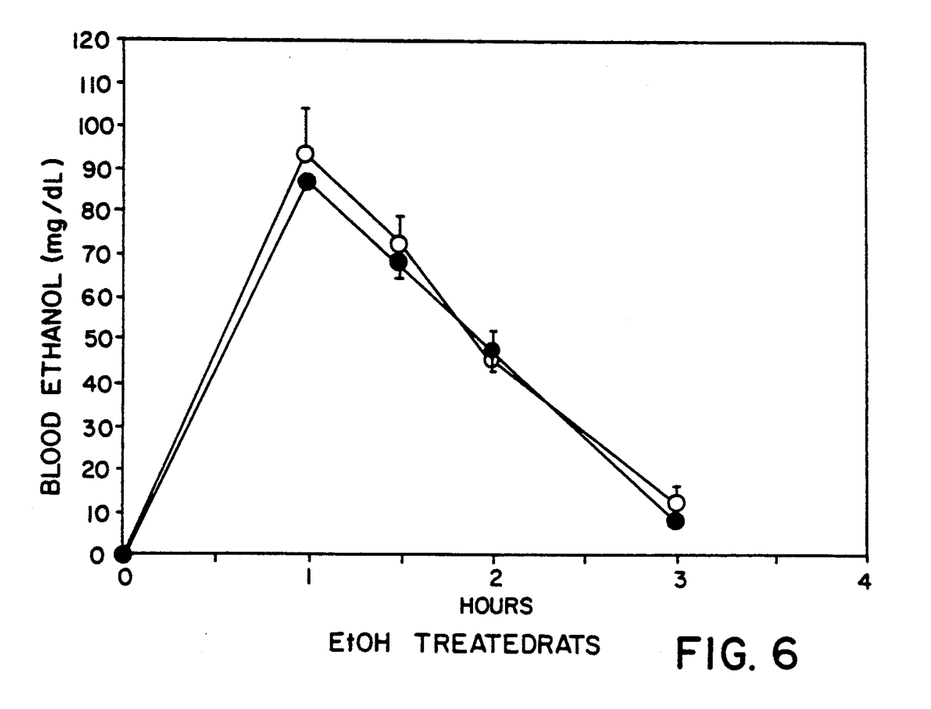
FIG. 6 is a diagram illustrating the concentration of ethanol/time profile by gas chromatographic analysis of blood, and eye vapour analysis, respectively, in ethanol-treated rats.

These animals had been fed on an ethanol-containing liquid diet for 4 weeks for different experimental purposes in our laboratory and were withdrawn from ethanol 5 days before the study. The rats, weight 274±12 g were given ethanol orally on the day of the study as above. Blood samples and eye vapor measurements were taken over three hours. The results are illustrated in FIG. 6.

Calculation of Blood Alcohol Concentration from Eye Vapor Response

The millivolt response from the eye was compared with a standard curve obtained from aqueous ethanol solutions. The standard curve was obtained from a correlation of the log of the concentrations and the millivolt response measured above 1 ml solutions in 20 ml scintillation vials at 29.5° C. The concentrations obtained from this calculation were multiplied by 0.85 to account for the differences in water content between blood and pure water.

Normal Rats-Lachrymal Fluid

Male, Sprague-Dawley rats, weighing 250-270 g were given ethanol as above. Blood samples (9.57 $\mu$l) were taken from the tail vein and added to saturated salt water (250 $\mu$l) in a head space vial. Lachrymal fluid samples (typically 3 $\mu$l) were obtained in a capillary tube (5 $\mu$l) while the animals were under ketamine anesthesia (80 mg/kg, intramuscularly, plus 15 mg/kg as needed). The exact volumes of these samples were determined from the length of liquid in the capillary tubes. These samples were also added to saturated salt water in a head space vial. The samples were obtained from 1 to 4 hours after ethanol administration.

Determination of Tail Vein Blood and Lachrymal Fluid Ethanol Concentrations

Blood ethanol concentration was determined by head space gas chromatography by methods known in the art.

Calculation of Metabolic Rates

The rectilinear portions of the plasma ethanol concentration versus time profiles were identified from the individual plots. Least squares regression analyses yielded the intercepts on the abscissae which were divided by the dose to give ethanol metabolic rates in mg/kg/hr.

The concentration versus time profiles are shown in FIGS. 5 and 6. It will be apparent that throughout the study periods, there is good agreement between the concentrations of ethanol obtained by gas chromatographic analysis of blood and by eye vapor analysis. As a consequence, the metabolic parameters obtained by the two methods for the groups of animals are also in good agreement. For the normal rats, the metabolic rates were calculated to be 241±7 and 234±9 (s.e.m.) mg/kg/hr by blood and eye vapor analysis, respectively. For the ethanol treated animals the comparable results were 318±7 and 302±13 mg/kg/hr. Using all of the individual data points, the correlation of blood ethanol concentrations obtained by the two methods yields: correlation coefficient=0.92, slope=0.99, intercept=4.2 mg/dl, n=61, range 0-98 mg/dl.

Figure 7:
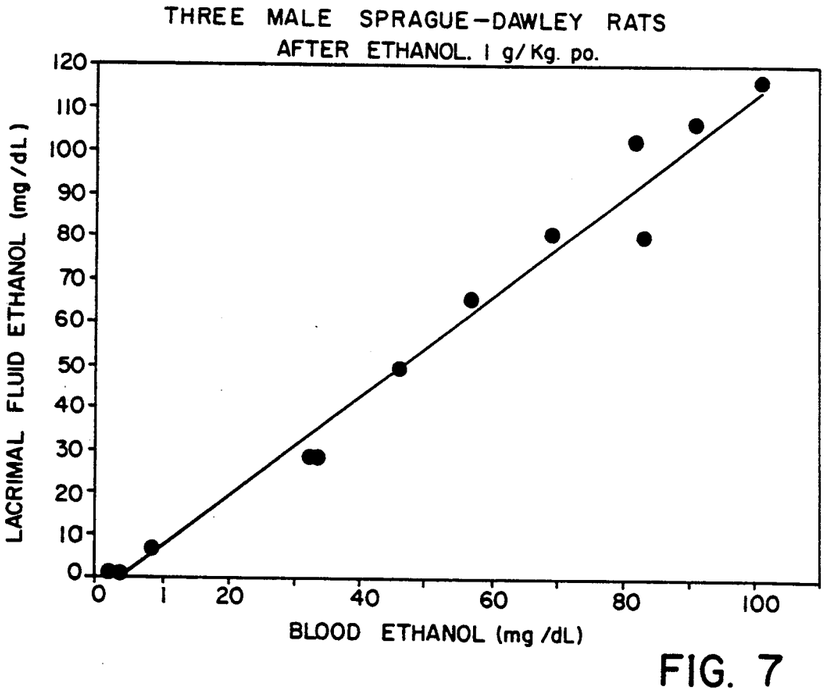
FIG. 7 is a diagram illustrating the concurrence between the ethanol concentration in blood and lachrymal fluid in three male Sprague-Dawley rats.

The correlation of ethanol concentration in blood and lacrimal fluid are shown in FIG. 7 where correlation co-efficient=0.99, slope=1.18, 1/slope=0.85, intercept=−5.0 mg/dl, n=12. The ratio of ethanol concentrations in the two fluids is given by the slope of the correlation or the reciprocal of the slope. The reciprocal of the slope is the same as the ratio of the water contents of lachrymal fluid (approximately 100%) and blood (85% for humans).

EXAMPLE II

Rabbits: First Study

Figure 8:
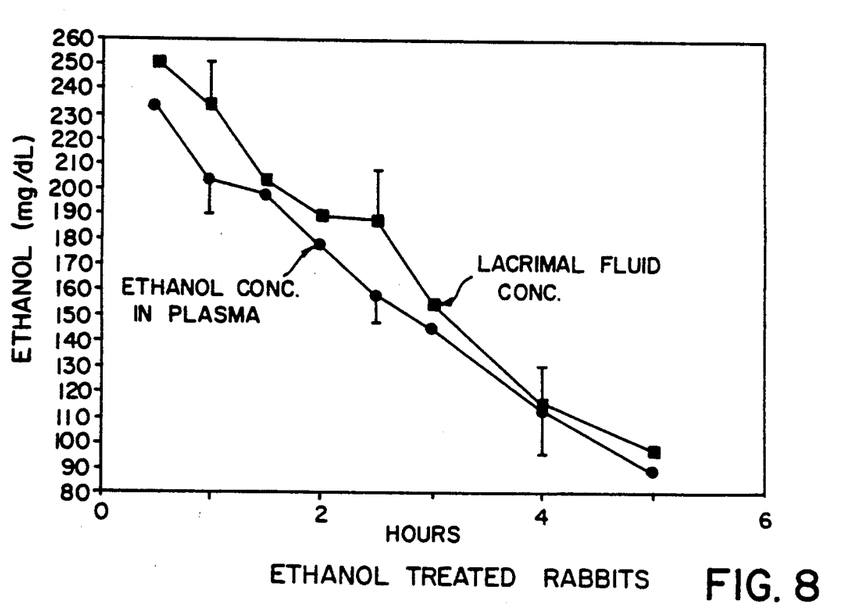
FIG. 8 is a diagram comparing the ethanol concentration/time in plasma (circles) and lachrymal fluid (squares) after ethanol administration to 4 New Zealand white rabbits.

Four, male, New Zealand White rabbits received ethanol (6 g/kg) by an intravenous bolus in a marginal ear vein. Heparinized blood samples (0.1 mL) were obtained from the opposite ear and centrifuged to yield plasma. Samples (0.01 mL) of lachrymal secretion were collected by micropipette from the lower conjunctival sac. The times of the samples as indicated in FIG. 8 were taken over 5 hours.

Analysis of Ethanol in Plasma and Lachrymal Fluid

Ethanol concentrations were determined either by known injection gas chromatography or by head space gas chromatography techniques.

Rabbits: Second Study

Figure 10:
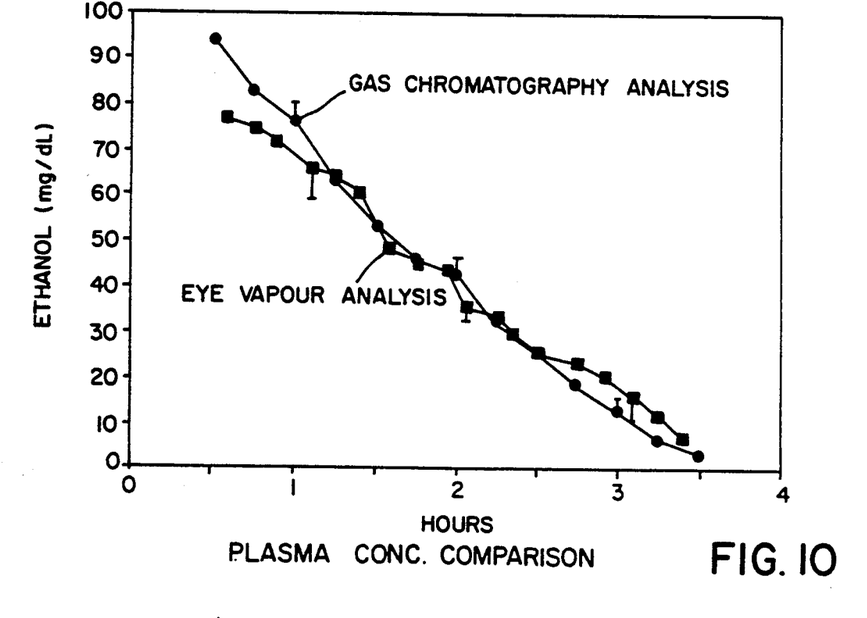
FIG. 10 is a diagram illustrating the ethanol concentration/time in plasma obtained by gas chromatography (circles) and by eye vapor analysis (squares) in 4 New Zealand white rabbits.
Figure 11:
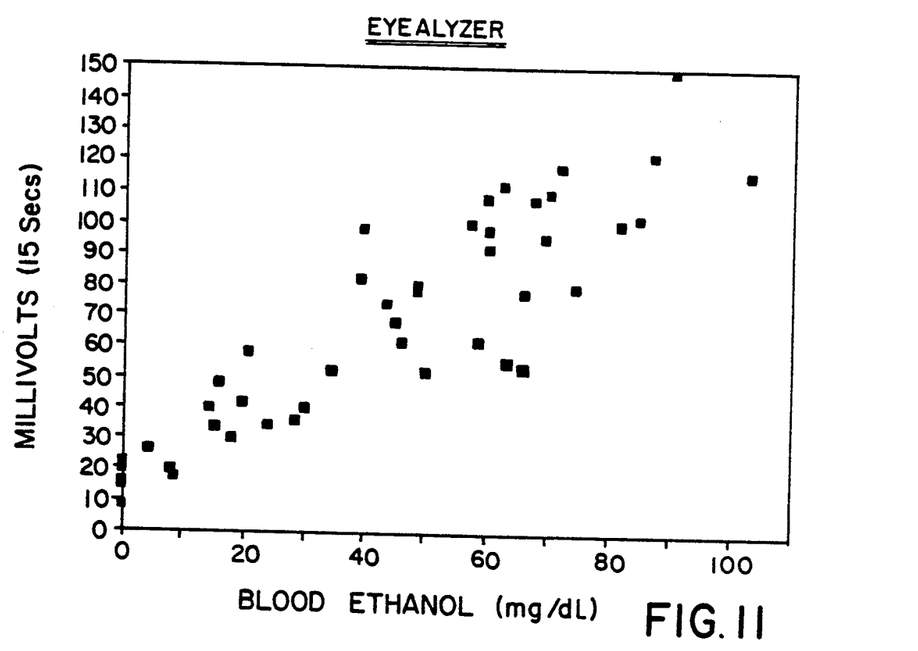
FIG. 11 is a diagram illustrating the relationship between a 15 second millivolt response on the eye and blood ethanol when measured in accordance with the present invention.
Figure 12:
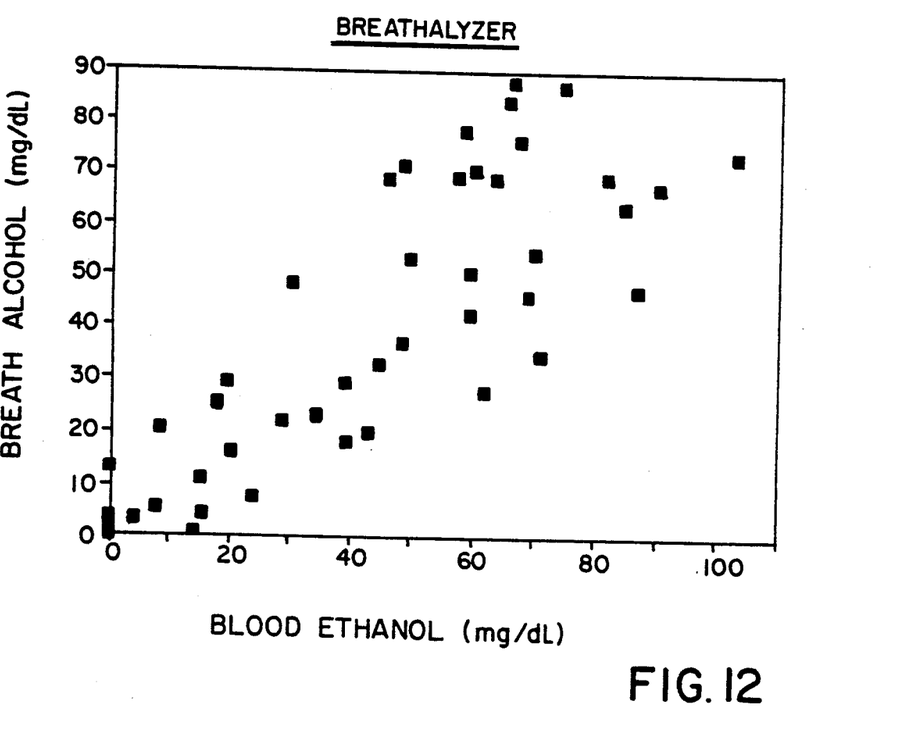
FIG. 12 is a diagram illustrating the relationship between breath alcohol and blood ethanol employing a conventional breathalyser machine.
Figure 13:
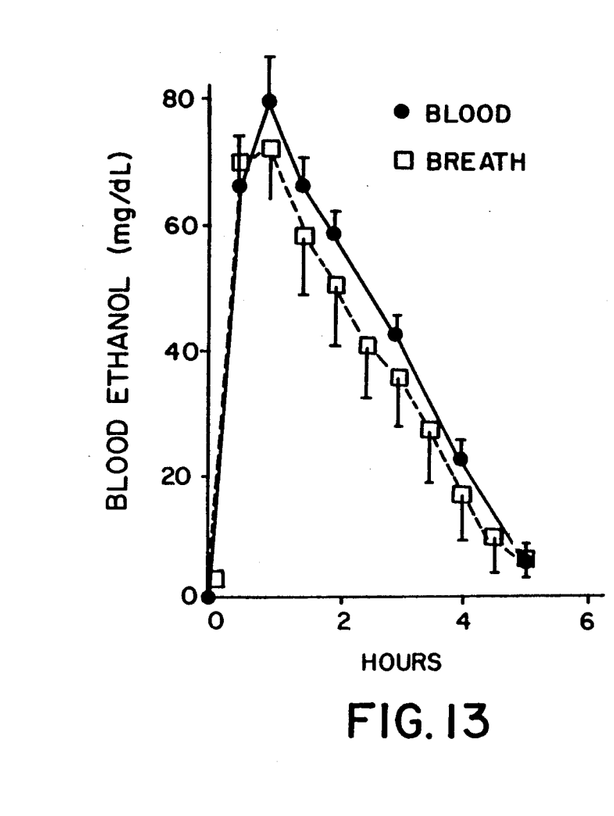
FIG. 13 is a diagram illustrating the relationship between blood ethanol level/time as measured by gas chromatography in the blood (circles) and in the breath as measured by breathalyser (squares)
Figure 14:
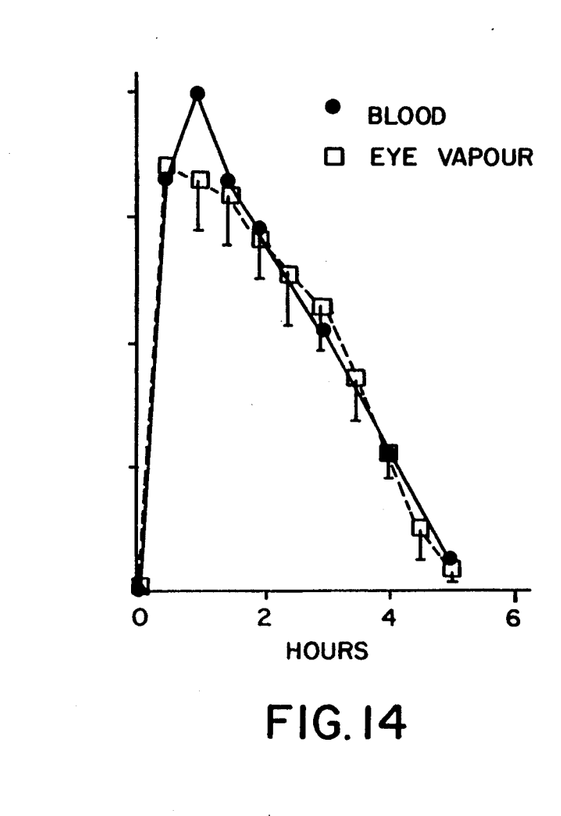
FIG. 14 is a diagram illustrating the relationship between blood ethanol level/time as measured by gas chromatography (circles) and in the eye vapor as measured by the method of the present invention.

Six, male, New Zealand White rabbits received ethanol (about 750 mg/kg, Table 1) by an intravenous bolus in a marginal ear vein. Blood samples and 30 second eye measurements were taken over 3.5 hours as indicated in FIG. 10.

Analysis of Ethanol in Vapor

For the ethanol vapor determination eyepiece 9 was used to hold the sensor in position, the eyepiece had a volume of approximately 24 mL. For the measurements, the sensor was placed in the top of the eyepiece (leaving a volume of 23 mL.) and the bottom edge was placed around the eye of the rabbit. The sensor was activated for 30 seconds after which time the millivolt response was noted.

Calculation of Plasma Concentration From Eye Measurements

Figure 9:
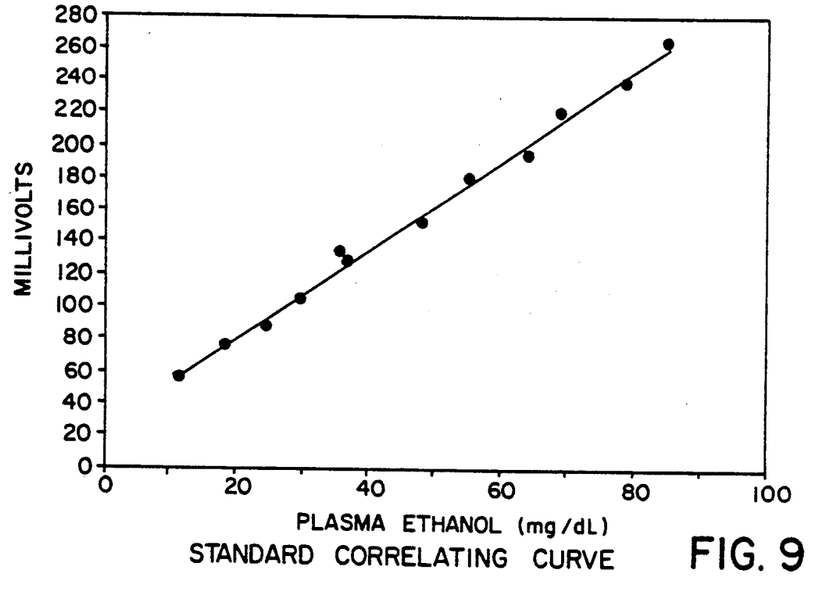
FIG. 9 is a diagram of a standard curve illustrating the correlation between plasma concentration of ethanol and eye vapor response in millivolts with the basal millivolt response substracted.

The results of the first two rabbits studied were used to calculate plasma concentrations from ethanol eye vapor responses in the other four animals. The standard curve (FIG. 9) was obtained by correlating points of the linear portion of the ethanol plasma concentration versus time curves with the coincident eye vapor responses that were measured in millivolts. This standard curve was then used for the other four rabbits to give estimated plasma concentrations from the eye measurements. A comparison of the actual plasma concentrations and estimated plasma concentrations is shown in FIG. 10.

Calculation of Metabolic Parameters

The rectilinear portions of the plasma ethanol concentration versus time profiles were identified from the individual plots. Least squares regression analyses yielded the slopes of the lines and intercepts on the abscissae. The slopes gave the clearances of ethanol in mg/dL/h while the abscissae were divided by the doses to give ethanol metabolic rates in mg/Kg/h. These results are shown in Table 1 below.

TABLE 1

| | | | Comparison of metabolic parameters derived by the two methods | | | |
|---|---|---|---|---|---|---|
| Rabbit | | | GC plasma analysis | | Eye ethanol vapor analysis | |
| No. | Weight (kg) | Dose (mg/Kg) | −Slope (mg/dL/h) | Metabolic rate (mb/Kg/h) | −Slope (mg/dL/h) | Metabolic rate (mg/Kg/h) |
| 3 | 2.5 | 754 | 29.7 | 234 | 21.2 | 200 |
| 4 | 2.6 | 750 | 29.3 | 234 | 25.9 | 217 |
| 5 | 2.4 | 771 | 31.4 | 232 | 30.9 | 207 |
| 6 | 3.2 | 808 | 25.6 | 207 | 26.5 | 215 |
| Mean | | | 29.0 | 226 | 26.1 | 210 |
| S.D. | | | 2.4 | 13 | 4.0 | 8 |

EXAMPLE III

Six alcoholic liver disease patients were given 0.5 g/Kg of ethanol intravenously over 45 minutes.

The blood ethanol level, breath alcohol level and eye vapor alcohol level were determined. In the case of blood ethanol at hourly intervals and in the latter two cases at half-hourly intervals in the same manner as previously described in Examples I and II. The blood ethanol level was determined by gas chromatography; the breath alcohol level was determined using a breathalyser (A.L.E.R.T. model manufactured by Alcohol Countermeasures Inc.) In the case of the eye vapor this was accomplished by holding the sensor eyepiece over the subject's open eye, with the eyepiece edges in contact with the subject's face for fifteen seconds and the fifteen second millivolt response was obtained. The results are shown in FIGS. 11, 12, 13 and 14.

It will be observed that the correlation between the eye vapor results and the breathalyser results in these various experiments indicate that a more accurate result than the breath test and results which are statistically acceptable and comparable with gas chromatography without the attendant awkwardness and difficulty.

The embodiments of the invention in which an exclusive property or privilege is claimed are defined as follows:

1. A method of detecting ethanol in lachrymal fluid which comprises enclosing an open eye of a subject in a chamber to define a space above the eye, providing an ethanol vapor sensor into the space of the chamber in a spaced relation to the eye; calibrating said sensor; and measuring the ethanol concentration in space above said lachrymal fluid exuded by the eye.

2. The method of claim 1 wherein said measuring step follows said enclosing step by a time sufficient for the concentration of alcohol in the vapors within said chamber to relate to the concentration of alcohol in the liquid lachrymal fluid of said eye in accordance with Henry'law.

3. The method of claim 1 further comprising the initial step of restraining said eye in an open state.

4. The method of claim 1 wherein said enclosing step includes the step of sealing an eyepiece against the face of said subject.

5. An apparatus for detecting alcohol levels in humans comprising:
   an eyepiece contoured to form a vapor confining chamber over the eye of a human subject; and
   an ethanol detecting sensor connected to said eyepiece to sample vapor from within said chamber.

6. The apparatus of claim 5 further comprising:
   means connected to said sensor for comparing said measured ethanol content with a reference to determine the blood alcohol level of said human subject.

7. The apparatus of claim 5 wherein said eyepiece has a substantially vapor impervious wall defining a chamber with lower and upper open ends, said lower open end having an edge conformable with the face contour of the subject, said upper open end being shaped to receive in use the ethanol detecting sensor, in substantially sealed spaced relation with the eye of the subject.

8. An apparatus as claimed in claim 7 wherein said wall defines a frusto-conical chamber.

9. An apparatus as claimed in claim 7 wherein said lower end of said wall has a cushion mounted therearound.

10. A method of determining the blood alcohol level of a person comprising the steps of:
sampling vapors of lachrymal fluid from an eye of said person; and
measuring the ethanol vapor content of said sampled lachrymal fluid vapor.

11. The method of claim 10 further comprising the step of:
comparing said measured ethanol content with a reference to determine the blood alcohol level of said person.

12. The method of claim 10 further comprising the step of:
enclosing a chamber about said eye of said person to define a confined space adjacent said eye, said sampling step including the step of sampling said vapors from a gas within said confined space.

13. The method of claim 12 wherein said eye is open.

14. The method of claim 12 further comprising the initial step of restraining said eye in an open state.

15. The method of claim 12 wherein said measuring step follows said enclosing step by a time sufficient for the concentration of alcohol of the vapors within said chamber to relate to the concentration in alcohol in the liquid lachrymal fluid of said eye in accordance with Henry's law.

16. The method of claim 15 wherein said time is at least approximately fifteen seconds.

17. The method of claim 15 wherein said eye is open.

18. The method of claim 12 wherein said chamber is enclosed with an eyepiece having an open end, and with a portion of the face of said person which includes said eye of said person closing said open end.

19. The method of claim 18 wherein said eye is open.

20. The method of claim 18 wherein said eyepiece is a tube having a second open end and said chamber is further formed by closing said second open end with structure which includes an ethanol detecting sensor, said measuring step being performed with said sensor.

* * * * *